US00PP20611P3

(12) United States Plant Patent
Maillard et al.

(10) Patent No.: US PP20,611 P3
(45) Date of Patent: Dec. 29, 2009

(54) PEACH TREE NAMED 'JULIEPRETTY'

(50) Latin Name: *Prunus persica*
Varietal Denomination: Juliepretty

(75) Inventors: Laurence Maillard, Elne (FR); Arsene Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 207 days.

(21) Appl. No.: 11/434,905

(22) Filed: May 17, 2006

(65) Prior Publication Data

US 2006/0265798 P1 Nov. 23, 2006

(51) Int. Cl.
*A01H 5/00* (2006.01)

(52) U.S. Cl. ..... Plt./197

(58) Field of Classification Search ..... Plt./197
See application file for complete search history.

(56) References Cited

U.S. PATENT DOCUMENTS

2006/0265798 P1 * 11/2006 Maillard et al. ..... Plt./197
2006/0265799 P1 * 11/2006 Maillard et al. ..... Plt./197
2007/0250972 P1 * 10/2007 Maillard et al. ..... Plt./198
2007/0250973 P1 * 10/2007 Mailllard et al. ..... Plt./198

* cited by examiner

*Primary Examiner*—Wendy C. Haas
(74) *Attorney, Agent, or Firm*—Westerman, Hattori, Daniels & Adrian, LLP.

(57) ABSTRACT

A new and distinct variety of peach tree, denominated 'JULIEPRETTY', has an appealing fruit with a long shelf-life both on the tree after growth completion and after harvesting, a round shape, an orange yellow flesh which tastes aromatic, and a skin colored with a red blush over a red-orange ground.

2 Drawing Sheets

Botanical classification: *Prunus persica* L. Batsch—Yellow peach.

Variety denomination: 'JULIEPRETTY'.

BACKGROUND OF THE VARIETY

The present invention relates to a new and distinct variety of *Prunus persica* L. Batsch yellow peach tree. This new tree, named 'JULIEPRETTY', produces very long lifetime, good eating quality, clingstone fruit for fresh market in August in the 66—Pyrénées Orientales departement—France. Contrast is made to 'MAILLARGOOD' (unpatented) 'JULIENICE' (U.S. Plant patent application publication No. 20060265799) and 'O HENRY MERCIL' (U.S. Plant Pat. No. 4,399) peaches, standard varieties, for reliable description. 'JULIEPRETTY' is a promising candidate for commercial success in that its fruit has an appealing appearance with a red blush color over an orange ground color, a round shape, an orange yellow flesh which tastes aromatic. Moreover, fruit has very long shelf-life both on the tree after growth completion and after harvesting.

ORIGIN OF THE VARIETY

'JULIEPRETTY' peach tree originated in a cultivated area of the south of France, in the 66—Pyrénées Orientales departement—France where it was tested. This place is under a Mediterranean climate in a temperate area characterized by irregular and low precipitation with drought in summer, high temperatures all year long. The 'JULIEPRETTY' variety was obtained by controlled sowing of a seed resulting from an open-pollination of the 'MAILLARGOOD' (unpatented) variety. 'JULIEPRETTY' was provisionally designated and tested as 02.04.55 PJ and is registered at the Official Catalogue of the Agriculture Ministry of the French Republic Dec. 29, 2004 under No. 1016562. The new variety was obtained from open-pollination and is propagated by grafting. It has been determined to have unique tree and fruit characteristics making it worthy for commercial fresh fruit production. There are no known effects of this standard rootstock on this scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées Orientales departement, France.

SUMMARY OF THE VARIETY

The new and distinct variety of peach tree blooms in March at Perpignan in the Pyrénées Orientales department, France. More particularly, it blooms 3 days before the 'MAILLARGOOD' variety, between $6^{th}$ and $20^{th}$ of March.

The first fruit of 'JULIEPRETTY' ripens in August at the same time as the first fruit of 'O HENRY MERCIL'. More particularly, it approximately ripens between August $16^{th}$ and $25^{th}$.

DESCRIPTION OF THE DRAWINGS

In the accompanying drawing, which are as nearly true as it is reasonably possible to make in a colour illustration of this type.

DETAILED BOTANICAL DESCRIPTION

Figure 1:
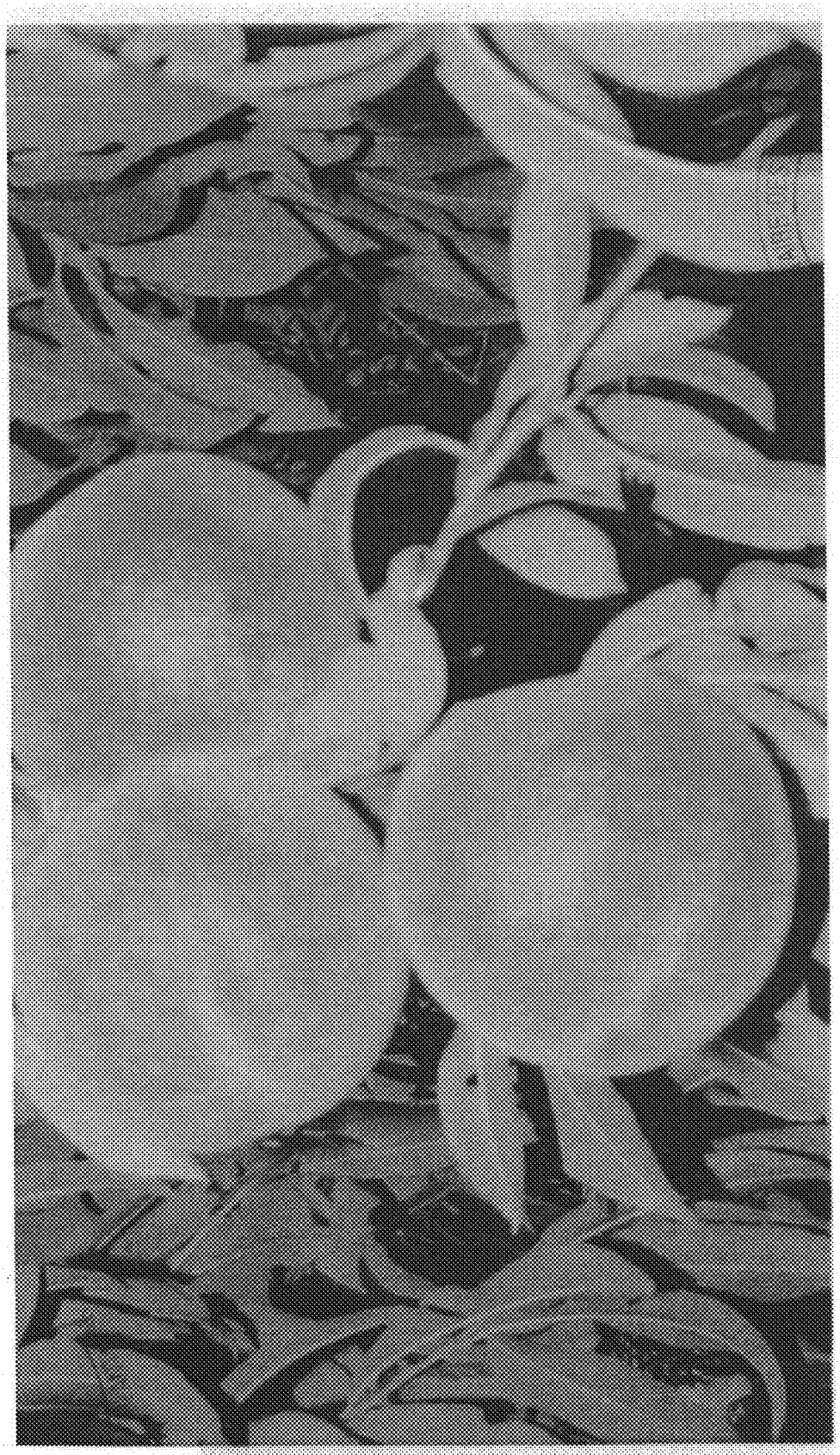
FIG. 1 is a colour photograph which shows the flesh of the fruit of the new variety 'JULIEPRETTY'.
Figure 2:
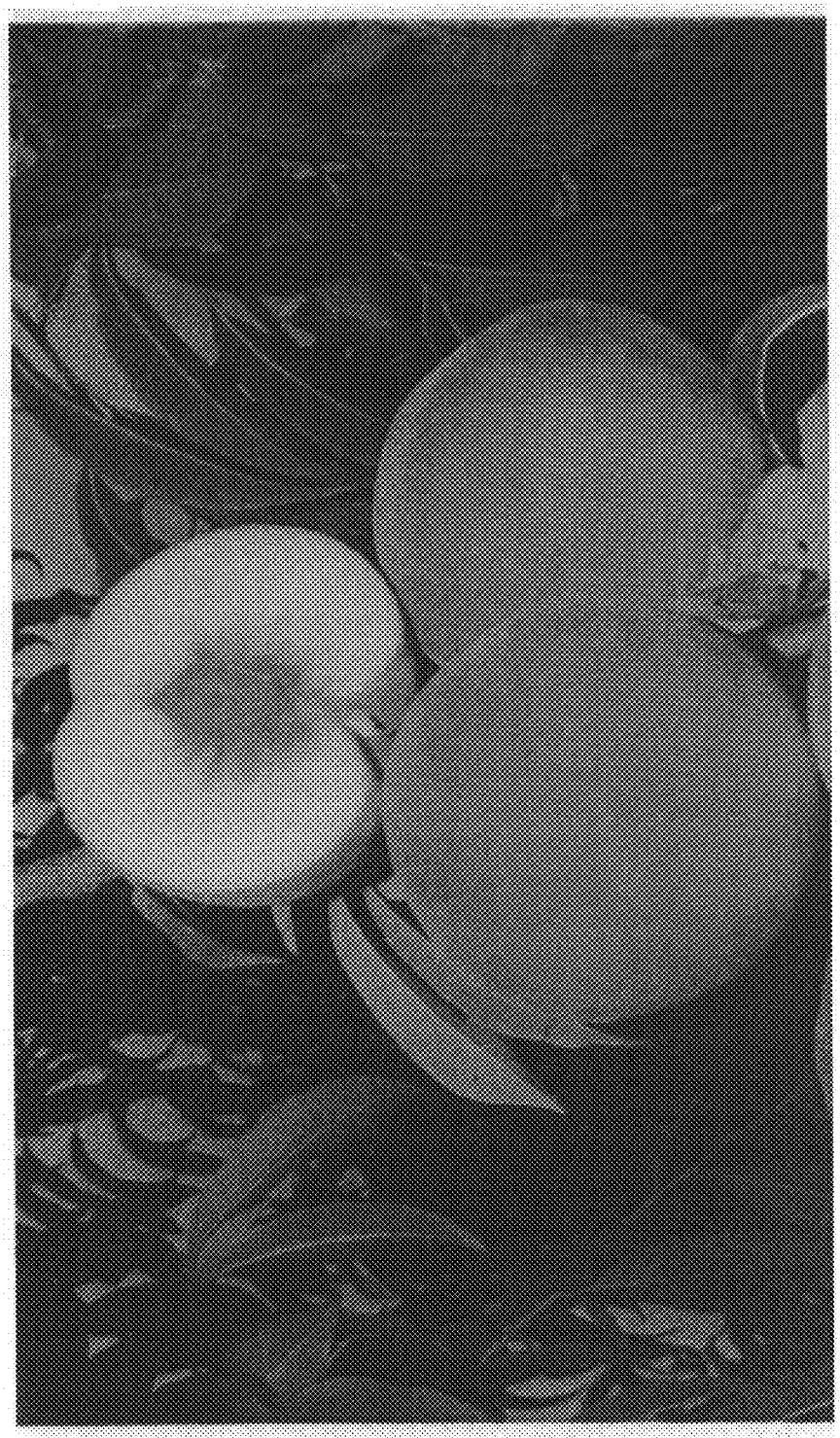
FIG. 2 is a colour photograph which shows a typical specimen of the fruit of the new variety 'JULIEPRETTY'.

The tree, flowers, and fruit may vary in slight detail due to variations in soil type, cultural practices, and climatic condition. The potential for commercial production of fresh fruit by 'JULIEPRETTY' is high, due to its appealing round coloured shape and its balanced and aromatic taste.

Trees are vigorous and medium stature half-standing in a semi-spread out aspect. The flowering shoot is present excluding brushwoods side away from sun. Flowering begins medium in springtime. The type of flower is showy with medium petal size. Petals are pale pink. Leaf glands are present and reniform. Time of maturity for consumption is medium. The fruit flesh is yellow. The stone is medium size and the flesh is adherent.

Compared to 'MAILLARGOOD' variety, 'JULIEPRETTY' blooms 4 days before and has an earlier time of maturity, 7 to 10 days before. The flesh of 'JULIEPRETTY' is orange yellow whereas 'MAILLARGOOD' flesh is yellow with red pigmentations. 'JULIEPRETTY' tastes balanced whereas 'MAILLARGOOD' tastes semi acidulated.

Compared to 'O HENRY MERCIL' variety, 'JULIEPRETTY' has the same date of maturity and same high productivity. 'JULIEPRETTY' tastes balanced whereas 'O HENRY MERCIL' tastes acidulated. 'JULIEPRETTY' fruit skin color is given by a red blush on 80 to 90 % of the fruit skin surface with an orange yellow ground color, whereas 'O HENRY MERCIL' fruit skin color presents a red blush on only 70 to 80% of the fruit skin surface with a green yellow ground color.

Compared to 'JULIENICE' variety, 'JULIEPRETTY' has absolutely the same taste but has an earlier maturity, 8 days before 'JULIENICE'.

DETAILED DESCRIPTION

Referring more specifically to the pomological details of this new and distinct variety of peach tree, the following has been observed, if not differently specified, during the second fruiting season under the ecological conditions prevailing at the orchards located in Elne, in the Pyrénées Orientales departement, France. All observations have been done on rootstock cultivar. The rootstock was a FRAN INRA MONTCLAR (unpatented) tree. All major color code designations are by reference to The R.H.S. Color Chart (Fourth Edition) provided by The royal Horticultural Society of Great Britain.

TREE

Generally: Considered medium to large as compared to other common commercial peach cultivars ripening in the medium season of maturity. The tree size the first year was approximately 280 cm. The tree was pruned during each following dormant season to a height of approximately 250 cm. Current season shoots growth could reach 80 cm. So the tree size from the second year (second and next years) reached a final height of 330 cm with current season shoots length comprised.

Spread: Approximately 200 cm with a cylindrical shape. The whole orchard was oriented to a central leader organisation, with tree lines spaced of 4.0 meters and trees spaced of 1.0 meter in a same tree line. As a result, the orchard contains 2500 trees by hectare.

Vigor: Considered moderately vigorous.

Productivity: Very Productive. Fruit set is spaced by thinning to develop the remaining fruit into the desired market sized fruit. The number of the fruit set varies with the prevailing climatic conditions, and cultural practices employed during the bloom period, and is therefore not distinctive of the present variety.

Bearer: Very regular. Thinning of 1 fruit on 4 was necessary every year during the past 5 years. Thinning must remain slight because of fruit magnifying potential.

Form: The 'JULIEPRETTY' variety has naturally a semi-spread shape.

Density: Considered dense.

Hardiness: The present tree was grown and evaluated in France. The variety appears to be hardy under typical central Pyrénées Orientales departement climatic conditions. Experimentations on different sites with winter chilling requirement comprised between 350 and 1200 hours showed a good behavior of the tree in all cases. Ascertained temperatures as low as −12 degrees Celsius caused no damages to the tree. The tree was also very resistant to frosty springtime weather.

TRUNK

Diameter: Approximately between 6.0 and 7.0 cm in diameter when measured at a distance of approximately 30 cm above the soil level.

Bark texture: Considered slightly rough, with folds of papery scarfskin being present.

Lenticels: Numerous lenticels are present. The lenticels range in size from 3 to 4 mm in width, and around 1.5 mm in height.

Lenticel colour: The outside of lenticels has a silver-grey color (varying from RHS Grey 201 D to RHS Black 202 D), whereas the inside is considered brown (RHS Greyed Orange 166B).

Bark colouration: The bark has a silver-grey color a little darker than the lenticels (varying from RHS Grey 201 C to RHS Black 202 C).

BRANCHES

Size: Mature branches as well as current season shoots are medium to thick for the variety.

Diameter: Average as compared to other peach varieties. The current season shoots have a diameter from 4.0 to 10.0 millimeters, and branches of trees have a diameter comprised between 25.0 and 32.0 millimeters.

Surface texture: Average, wood which is several years old has no furrowed appearance.

Crotch angles: Primary branches are considered variable, but the crotch angles are generally between 60 and 70 degrees from the horizontal axis. This particular characteristic is not considered distinctive of the variety, however.

Current season shoots:

*Surface texture.*—Substantially glabrous.

Internode length: Generally 20.0 to 24.0 millimeters.

Colour of mature branches: Medium grey-brown (varying from RHS Grey Brown 199 C to Grey Brown 199 B).

Current seasons shoots:

*Colour.*—The color of new shoot tips is considered a light green (varying from RHS Green 143 C to D) on lower part of new shoot tips, whereas the upper part is colored in reddish brown (varying from RHS Greyed Red 182 B to C), darkening when more exposed to the sun.

LEAVES

Size: Considered medium to large for the species. Leaf measurements have been taken from vigorous, upright, current-season growth at approximately mid-shoot.

Leaf length: Approximately 160 to 186 millimeters without the petiole.

Leaf width: Approximately 35 to 40 millimeters.

Leaf base shape: Concave.

Leaf form: Lanceolate.

Leaf tip form: Acuminate and small.

Leaf colour:

*Upper leaf surface..*—Dark Green (RHS Green 137 A).

*Lower surface.*—Medium Green (varying from RHS Green 137 B to 137 C).

Leaf texture: Smooth and glabrous.

Leaf venation: Pinnately veined.

Mid-vein:

*Colour.*—Light green (varying from RHS Yellow Green 144 D to 144 C).

Leaf margins: Slightly undulating.

Form: Considered slightly dentate.

Uniformity: Leaves are isolated or grouped by 2 or 3. In this last case, it is found one leaf of normal size with one or two smaller leaves (size-reduction of 50% and more).

Leaf glands:

*Size.*—Considered medium, between 1.5 and 2.0 millimeters.

*Number.*—Generally between 3 and 4: 2 on the petiole and 1 to 2 on the leaf.

*Type.*—Reniform.

*Colour.*—On young leaves, leaf glands color is considered a pale green (RHS Green 145 B). On older leaves, leaf glands color turns to a dark brown (varying from RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Generally: Observations have been made on Mar. 2, 2008.

Flower buds:

*Generally.*—At pre-floral stage of development, the floral buds are conic in form with a round tip. Their form is evolving until blooming, with variables dimensions. Just before blooming, floral buds are approximately 10.0 millimeters wide and approximately 18.0 millimeters long.

Flower buds:

*Colour.*—This characteristic is dependent upon the proximity to bloom. At pre-floral stage of development, the bottom of the flowers buds, formed by sepals, is of purple-brown color (RHS Greyed Purple 183 A); the corolla, formed by petals, is generally of pale pink color (varying from RHS Red Purple 65 A to B). Petals color shows an evolution until the end of flowering. The buds are considered hardy under typical central Pyrénées Orientales departement climatic conditions.

Hardiness: No winter injury was noted during the last several years of evaluation in the central Pyrénées Orientales departement, with winter temperatures as low as −12 degrees Celsius in January. The current variety has not been intentionally subjected to drought or heat stress, but the variety showed a good resistance in orchard to temperatures up to 42 degrees Celsius with an average temperature between 28 and 30 degrees Celsius during 3 weeks in summer.

Date of bloom: Generally March. The first bloom, observed on Feb. 27, 2002, was exceptionally early. Second and third bloom took place respectively on March 11, 2003 and Mar. 6, 2004.

Blooming time: Considered early-season in relative comparison to other commercial peach cultivars grown in the Pyrénées-Orientales departement, France. The date of full bloom is observed on March, more particularly between March $3^{th}$ and $18^{th}$. The date of bloom varies slightly with climatic conditions and cultural practices.

Duration of bloom: Approximately 15 days. This characteristic varies slightly with the prevailing climatic conditions.

Flower type: The variety is considered to have a showy type flower.

Flower size: Considered of medium size. Flower diameter at full bloom is approximately 33.0 to about 41.0 millimeters.

Bloom quantity: Considered abundant, approximately about 35 flowers per meter.

Flower bud frequency: Generally 2 flower buds appear per node, occasionally 1.

Petal size:

*Generally.*—Considered medium for the species.

Length: Generally about 21.2 millimeters.

Width: Generally about 19.8 millimeters.

Petal form: Rounded.

Petal count: 5.

Petal texture: Smooth and glabrous.

Petal colour: Pale Pink (varying from RHS Red Purple 69 A to B) when young, darkening with advancing senescence.

Fragrance: Slight.

Petal claw:

*Form.*—The claw is considered to have a conic form with a slighty rounded extremity.

*Length.*—Approximately 6.0 to 8.0 millimeters.

*Width.*—Approximately 5.0 to 6.0 millimeters.

Petal margins: Generally very slightly undulated.

Petal apex:

*Generally.*—The petal apices are generally entire at the tip, dome-shaped.

Flower pedicel:

*Length.*—Considered medium-long and having an average length of approximately 4.0 to 5.0 millimeters.

*Diameter.*—Considered average, approximately 2.0 millimeters.

*Colour.*—Brown to Light Brown (varying from RHS Grey Brown N199 B to C).

Floral nectaries:

*Colour.*—A flat yellowish orange (varying from RHS Greyed Red 178 C to D).

Calyx:

*Internal surface texture.*—Smooth and glabrous.

*Color.*—The outer surface of the calyx is considered of Purple-brown (RHS Greyed Purple 183 A) color.

Sepals:

*Surface texture.*—The outer surface has a short, fine pubescent texture.

*Size.*—Generally medium-sized.

*Colour.*—A Purple-brown (RHS Greyed Purple 183 A).

Average number of stamens per flower: Approximately 35 to 40 stamens per flower.

Anthers:

*Generally.*—Medium in length.

*Color.*—Orange-Yellow (varying from RHS Yellow Orange 16 A to B). Anthers are becoming brown after maturity (RHS Greyed Purple Group 178 A).

Pollen production: Pollen is abundant, and has a yellow color (varying from RHS Yellow Orange 17 B to C). The present variety is considered self fruitful (self-pollinating).

Filaments:

*Size.*—Variable in length, approximately 11.0 to 17.0 millimeters in length. In all cases filament's length is superior or equal to pistil's length.

Color: Considered light pink (varying from RHS Red Purple 62 C to D) to darker pink (varying from RHS Red Purple 73 A to B) with advancing senescence.

Pistil:

*Number.*—Generally 1.

*Generally.*—Average in size.

*Length.*—Approximately 15.0 to 17.0 millimeters including the ovary; Smaller or equal to filament's length.

*Colour.*—Considered a very pale green (varying from RHS Yellow Green 150 D Group to RHS Yellow Green 151 D Group).

*Surface texture.*—The variety has a glabrous pistil, but the ovary presents a pubescence.

FRUIT

Maturity when described: Very firm ripe condition (shipping ripe).

Date of first picking: Aug. 16, 2002. The date of harvest varies slightly with the prevailing climatic conditions.

Date of last picking: Aug. 25, 2002, only 2 harvests in 10 days were necessary.

Size:

*Generally.*—Considered large to very large, and uniform.

Average cheek diameter: Approximately 73.0 to 75.0 millimeters

Average axial diameter: Approximately 65.0 to 70.0 millimeters

Typical weight: Approximately between 260.0 and 290.0 grams. This characteristic is high dependent upon the prevailing cultural practices, and therefore is not particularly distinctive of the variety.

Fruit form:

*Generally.*—Rounded and very slightly flat. The fruit is generally uniform in symmetry, viewed from pistil end.

Fruit suture: Shallow, extending from the base to the apex. No apparent callousing or stitching exists along the suture line.

Suture:

*Colour.*—This has generally a color similar to the fruit skin color, a red blush (varying from RHS Greyed Purple 183 A to B) on a Red-orange (varying from RHS N34A to N34B) ground color.

Ventral surface:

*Form.*—Smooth.

Apex: Slightly depressed, very small, not prominent.

Base: Shallow.

Stem cavity: Average depth of the stem cavity is about 15 mm. Average width is about 18 to 20 mm.

Fruit skin:

*Thickness.*—Considered thick and strong, and tenacious to the flesh to moderately tenacious to the flesh depending on stage of maturity.

*Texture.*—Very slightly pubescent.

*Taste.*—Balanced and sweet.

*Tendency to crack.*—Generally none observed.

Colour:

*Blush colour.*—This blush colour is generally red (varying from RHS Greyed Purple 183 A to B). The red blush covers 80% to 90% of the fruit skin surface. The percentage of the blush on the fruit skin surface can vary, and is generally dependant upon the prevailing conditions under which the fruit was grown.

*Ground colour.*—Red-orange (varying from RHS Orange Red Group N34A to N34B) on 10 to 20% of the fruit skin surface.

Fruit stem: Medium in length, approximately around 7.0 millimeters.

Diameter: Approximately around 4.0 millimeters.

Colour: Pale green (varying from RHS Yellow Green 145A to 145 B).

Flesh:

*Ripens.*—Very evenly, homogenous, long shelf-life of the fruit.

*Texture.*—Very firm, very dense, juicy at harvest maturity stage.

*Fibers.*—Generally none observed.

*Aroma.*—Pronounced.

*Eating quality.*—Considered very good, aromatic.

*Flavor.*—Considered balanced. The Brix is superior to 13.0 degrees. Acidity is comprised between 9 and 12 meq/100ml. The flavor is considered aromatic. The flesh is juicy.

*Juice.*—Jucy to very juicy at complete maturity.

*Brix.*—Generally superior to 13.0 degrees. This characteristic varies slightly with the number of fruit per tree; prevailing cultural practices; and the surrounding climatic conditions, and can be much more higher.

*Flesh colour.*—Yellow (RHS Yellow Orange 16A) with a slight red pigmentation (varying from RHS Orange Red Group N34A to N34B) star-shaped around the stone.

STONE

Type: Clingstone.

Size: Considered medium to large for the variety. The stone size varies significantly depending upon the tree vigor, crop load and prevailing growing conditions.

Length: Approximately between 32.0 and 35.0 millimeters.

Width: Approximately between 24.0 and 27.0 millimeters.

Diameter: Approximately between 14.0 and 17.0 millimeters.

Form: Flat.

Base: Straight.

Apex:

*Shape.*—The stone apex is very prominent and sharp.

Stone Cavity: Considered of medium to large size, with dimensions corresponding to stone's dimensions.

Stone surface:

*Surface texture.*—The pit is transversely furrowed on its entire surface. Furrows are more pronounced toward the apex.

*Ridges.*—The surface texture is generally characterized by more prominent ridges along the ventral edges and is more prominent at the apical tip.

Ventral edge:

*Width.*—Around 2.0 mm.

Dorsal edge:

*Shape.*—Grooved.

Stone colour: The color of the dry stone is generally considered a light Orange Brown (RHS Greyed Orange 176 D) to a Red Brown (RHS Greyed Red 178 D).

Tendency to split: Splitting is absent or very low, depending on climatic conditions between blooming period and stone hardening.

Kernel:

*Size.*—The kernel is considered medium.

*Length.*—About 20.0 millimeters.

*Width.*—About 12.0 millimeters.

*Thickness.*—About 3.0 to 4.0 millimeters.

*Form.*—Considered flat and elliptic.

*Pellicle.*—Pubescent.

*Colour.*—The kernel skin is a light yellowish orange (RHS Greyed Orange 167 C) with darker strikes (RHS Greyed Orange 166 C). The almond is cream-white (RHS Orange Chite 159 D). The kernel and its embryo are mature at the time of fruit maturity.

Use: The subject variety 'JULIEPRETTY' is considered to be a peach tree of the medium season of maturity, and which produces fruit that are considered very firm, attractively coloured. Fruits are excellent for uncooked consumption, crunchy or at full maturity, and very aromatic. They are useful for both local and very long distance shipping, with a shelf life of few weeks after harvest.

Keeping quality: Good. Fruit stayed a little more than one week on tree before harvest and then, has stored well until 2 to 3 weeks after harvest at 2.0 degree Celsius. They have a slow maturation and a long shelf life both on the tree after growth completion and after harvesting without alteration.

Shipping quality: Considered good. The fruit of the new peach variety showed minimal bruising of the flesh or skin damage after being subjected to normal harvesting and packing procedures.

Resistance to insects and disease: No particular susceptibilities were noted. The present variety has not been shown to be very sensitive to powdery mildew, or conservation diseases and decay due to its thick and strong skin.

Although the new variety of peach tree possesses the described characteristics when grown under the ecological conditions prevailing near the town of ELNE, FRANCE, it should be understood that variations of the usual magnitude and characteristics incident to changes in growing conditions, fertilization, pruning, pest control and horticultural management are to be expected.

We claim:

1. A new and distinct variety of peach tree, as herein illustrated and described.

* * * * *